United States Patent [19]

Annen et al.

[11] 4,156,180
[45] May 22, 1979

[54] APPARATUS AND METHOD FOR DETECTING METABOLIC ACTIVITY

[75] Inventors: Phillip A. Annen, Mountain View; Takeshi Omura, Los Altos, both of Calif.

[73] Assignee: Bactomatic, Inc., Palo Alto, Calif.

[21] Appl. No.: 809,703

[22] Filed: Jun. 24, 1977

[51] Int. Cl.² ........................................... G01R 27/00
[52] U.S. Cl. .................................... 324/57 R; 324/64; 324/65 R; 324/71 R; 324/98; 195/103.5 R
[58] Field of Search ..................... 324/57 R, 64, 65 R, 324/58.5 A, 71 R, 98; 23/253 R, 230 B; 195/103.5 R

[56] References Cited

U.S. PATENT DOCUMENTS

| 2,870,430 | 1/1959 | Hancock | 324/57 R X |
| 2,891,217 | 6/1959 | Grieg et al. | 324/57 R |
| 3,419,799 | 12/1968 | Papadeas | 324/57 R |
| 3,443,226 | 5/1969 | Knight | 324/98 X |
| 3,448,380 | 6/1969 | Harrington | 324/58.5 A |
| 3,879,662 | 4/1975 | Barneck | 324/98 |
| 3,916,304 | 10/1975 | Roemer et al. | 324/65 R X |
| 3,984,766 | 10/1976 | Thornton | 324/65 R X |

FOREIGN PATENT DOCUMENTS

| 1143929 | 2/1963 | Fed. Rep. of Germany | 324/98 |
| 1254244 | 11/1967 | Fed. Rep. of Germany | 324/98 |
| 1236092 | 6/1971 | United Kingdom | 324/98 |
| 1287190 | 8/1972 | United Kingdom | 324/64 |
| 384071 | 8/1973 | U.S.S.R. | 324/98 |

*Primary Examiner*—Stanley T. Krawczewicz
*Attorney, Agent, or Firm*—Phillips, Moore, Weissenberger, Lempio & Majestic

[57] ABSTRACT

An apparatus and method for detecting metabolic activity in a medium which includes an electrical circuit suitable for passing electrical current through a medium which contains a suspected metabolic agent. The circuit includes means for generating a reference voltage. When metabolic activity occurs in the medium the voltage drop thereacross changes. To balance the changing voltage developed across the medium with the generated reference voltage, an adjustment of current has to be performed. By monitoring such adjustments, made electrically and automatically, there is a correlation made between those adjustments and the metabolic activity in the medium. Use of this apparatus and method allows large quantities of sample media to be tested for detection of metabolic activity rapidly, accurately and reliably.

40 Claims, 5 Drawing Figures

FIG-1

FIG_2

FIG_5

FIG_3

FIG_4

APPARATUS AND METHOD FOR DETECTING METABOLIC ACTIVITY

BACKGROUND OF THE INVENTION

This invention relates to a method and apparatus for detecting changes in voltage potential developed in a medium. More particularly, this invention pertains to a method and apparatus for detecting metabolic activity in a growth medium based upon changes of electrical characteristics, such as the impedance, of that medium.

As a means of making rapid and accurate measurements of various media to determine whether metabolic activity is occurring, and sometimes identifying and enumerating the particular microorganisms involved, it has become known to correlate changes of electrical impedance with such activity. By establishing a relationship between metabolic activity and change of an electrical characteristic, such as impedance, of the growth medium, tremendous savings in time to detect bacteria presence or other microorganism and/or cellular activity have been achieved along with greater accuracy and more reliable test results than in the known turbidity analysis tests or radiometric methods. Well conceived equipment such as described in U.S. Pat. No. 3,984,766 to Thornton now makes it possible to automatically measure impedance ratios of a pair of cells containing a selected medium, one medium of which contains a suspected microorganism contaminant. The changes of impedance ratios of the media are directly related to growth of a microorganism therein. By using a ratio of impedance it is possible to eliminate all the variables affecting impedance changes except organism growth; these influential variables include temperature fluctuations, gradual corrosion of electrodes, aging of the medium, medium changes due to absorption of gases, etc. Moreover, the Thornton equipment is capable of handling the testing of many samples rapidly, accurately and automatically.

Other devices have been described, for instance, by Ur in British Specification No. 1,299,363 and U.S. Pat. No. 3,699,437, but such devices neither have the capacity nor the automation and rapidity of measurement as does the Thornton equipment.

As this technique of measuring reactions of an electrical characteristic of a medium to indicate metabolic activity occurring therein becomes more acceptable to users and potential users, additional improvements in these type devices are being sought. These sought-after improvements include the capability to test hundreds, even thousands, of samples in one system while keeping space constraints under consideration; greater accuracy in characterizing not only the presence of microorganisms growing in a medium, but their identification, levels of concentration and susceptibility to antibiotics; the ability to lower the threshold at which to detect the presence of microorganisms; and a computer system to monitor a very large number of test samples to analyze various data inputs from each and provide the user with a variety of results including specific identification of microorganisms in the shortest time span.

One of the shortcomings of the Thornton system as described in U.S. Pat. No. 3,984,766, and other impedance measuring systems related to microorganism growth, is in the lack of ability to handle very large numbers of samples during one test. While it is explained in the Thornton patent that large numbers of cell pairs can be measured in that apparatus, a number of factors combine to realistically limit the actual number of cell samples which can be measured during one test: the electrical circuit, in which the source of electrical energy, the oscillator, is a constant voltage source across which each pair of cells is serially connected; the fact that each sample or specimen cell has a reference cell physically proximate thereto and electrically connected in the circuit; and as a number of pairs of cells accumulate, their physical presence removes them further from the source of electrical energy. In practice, the oscillator provides a given voltage to all of the pairs of cells in parallel with each other. It can be appreciated that with a fixed voltage souuce there will be differences of voltage "seen" across each cell pair, especially at the cells which are furthest in distance from the voltage source or as cells are added to be tested in the fixed voltage system. Consequently, true voltage readings are not attained across the cell pairs at increased distance from the source since the lengths of electrical leads provides a transmission loading effect. Proper voltage requirements are critical in this type of system because extremely small voltage changes in the cells are the indicative means of pinpointing microorganism growth. Clearly, with this type system accuracy and reliability of measurements are sacrificed when the number of samples in the system are sufficient to produce variations in or unequal voltages applied across those samples. Of course, closely packaged samples can reduce the effect of transmission loading, but at some point the space physically occupied by a large number of samples will produce a line length loading problem.

Moreover, it must be kept in mind that the Thornton system has a reference cell for every sample cell. Thus, double the space and electrical wiring is needed for every additional sample to be tested. While this system provides excellent results for a moderately large number of test samples, there is indeed room for improvement in many aspects of such a system in order to accommodate a very large number of samples, such as in the hundreds, to be monitored during a single test.

SUMMARY OF THE INVENTION

Many of the deficiencies noted above have been overcome by the new apparatus and method of present invention. In addition, the improvements achieved by the present invention lend themselves to automation so that rapid and accurate results can be produced and reproduced. Besides providing for accurate and time saving results, a significant advantage in this new invention is its ability to continuously monitor a very large number of test samples. This ability to handle such an amount of samples is accomplished without sacrificing the accuracy of electrical energy which is delivered to each test sample such as occurs in some prior art devices. In other words, the electrical energy delivered to each sample in the array of samples is consistent with that delivered to the others regardless of electrical line length and the transmission loading effect. Furthermore, since state of the art technology in this field continues to advance, the electrical devices and circuitry to eliminate the transmission loading effect can be assembled relatively inexpensively.

One of the benefits of having a system in which a very large number of samples can be tested at once is the reduction of time inefficiencies and periodic changes of samples to be tested. In addition, better control is achieved since, for example, the environmental changes (humidity, temperature, etc.) which may be prevalent when testing samples of a given batch in separate tests no longer have to be considered in a system where the entire batch can be accommodated in one complete test. Also, since electrical line loading effects have been eliminated, there is no need to crowd together all the test samples if the room is available to spread them out.

Besides the above advantages, the present invention provides for a computer interface feature so that various results can be monitored during and after the test, and many pieces of information can be gathered on the test samples based upon that which the programmer provides in coordination with the type of test being conducted. Some of these computer features shall be discussed hereinafter.

It can be seen that these advantages are highly desirable in the search for metabolic activity such as growth of microorganisms which may cause health and medical problems. Systems which allow a very large number of blood, urine and related clinical cultures to be tested can produce results in a very short time span; rapid detection assists in medical diagnosis of a problem and may lead to life-saving treatment that needs initiation as soon as possible. Besides clinical or hospital applications, the apparatuses of the present invention are available to users such as the food industry for performing assurance tests for quality and healthiness of products headed for the consumer market. A wide range of applications is foreseen for the apparatus of the present invention which includes those improvements noted above among others which the users thereof may find.

In accordance with the principles of the present invention the new apparatus detects changes in voltage drop across a medium. Included in this apparatus is a source of electrical energy and means for passing that electrical energy through a sample medium and developing a voltage across that medium. This medium is susceptible to changes in its voltage drop at a given current flow. In addition, this apparatus comprises means for generating an electrical reference signal in the form of a voltage. Means to measure the voltage developed across the sample and to compare the same with the reference voltage are also included. When the voltage drop across the sample changes to an amount different from the reference voltage, adjusting means alters the voltage developed across the sample media to closely approximate or balance same with the reference voltage. There is also means to detect and indicate the amount of adjustment of the voltage drop across the sample medium necessary to balance the voltage drop thereacross with the voltage of the reference signal.

This type apparatus is especially useful in detecting growth of one or more microorganisms in a growth medium. The sample medium contains a suspected metabolic agent such as a microorganism contaminant; the adjusting means alters the voltage developed across the sample growth medium, which changes in response to microorganisms growing in that medium, to closely approximate or balance the voltage drop across the sample with the reference voltage which remains substantially constant. Monitoring means correlates the amount of adjustment of the voltage drop across the sample with metabolic activity in that sample.

In the preferred embodiment of the present invention in which the apparatus detects growth of microorganisms in a medium, the means to adjust the voltage drop across the sample includes an electrical circuit with a variable current source which changes sufficiently to allow the voltage drop across the sample medium to closely approximate the reference voltage. Use of binary input information from a successive approximation register in conjunction with the variable current source provides the necessary voltage drop across the sample to closely approximate the reference voltage. In this embodiment it is also preferable to test a plurality of samples in succession or in random sequence to determine whether there is metabolic activity occurring in any of the samples. In addition, this preferred apparatus includes a computer in the electrical circuit which is programmed to indicate when microorganism growth in any sample has occurred amongst other significant pieces of data.

The present invention further consists of the methods of detecting changes in voltage drop across a medium, and, particularly, of detecting metabolic activity in a growth medium. In the preferred method of this invention the steps include applying electrical energy from a source through a sample of growth medium containing a suspected metabolic agent whereby a voltage is developed across such medium. An electrical reference signal which is proportional to the oscillator voltage is also generated. Measuring the voltage developed across the medium and comparing such voltage and the reference voltage to each other are sequentially accomplished. This aspect of the invention also comprises adjusting the voltage developed across the sample medium, which changes in response to metabolic activity in that medium, with the reference voltage which remains substantially constant. Monitoring the adjustment of the voltage developed across the sample to correlate that adjustment with a detection of metabolic activity is the final part of this novel method.

BRIEF DESCRIPTION OF THE DRAWINGS

These and other advantages, features and aspects of the invention will become apparent upon reading the following detailed description and upon reference to the accompanying drawings, in which.

While the invention will be described in connection with a preferred embodiment, it is understood that it is not intended to limit the invention to that embodiment. On the contrary, it is intended to cover all alternatives, modifications and equivalents as may be included within the spirit and scope of the described invention.

DETAILED DESCRIPTION OF THE INVENTION

Figure 1:
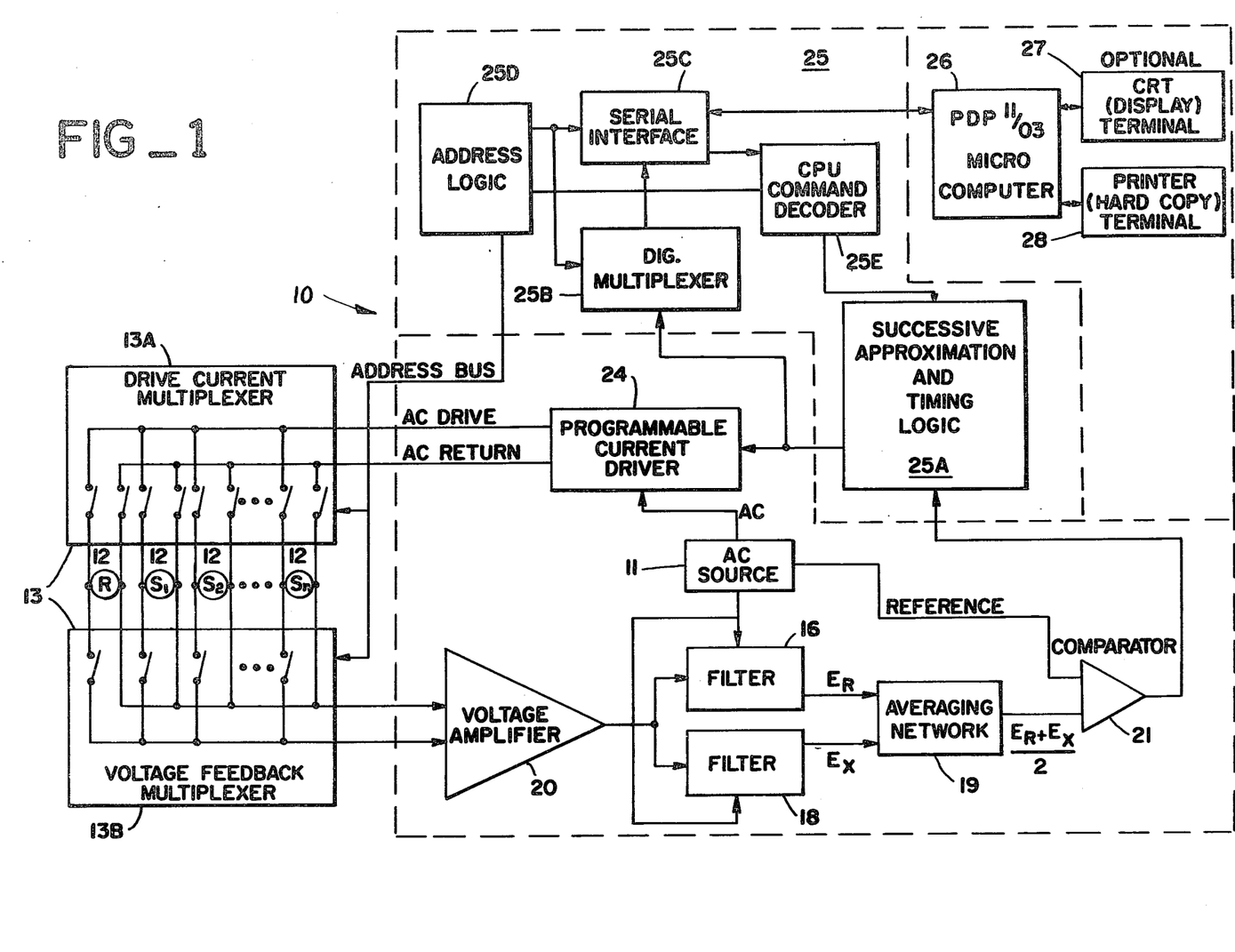
FIG. 1 is a block diagram schematically illustrating the inventive apparatus.

Adverting to the drawings in which a preferred embodiment is illustrated there is shown in FIG. 1 a block diagram containing the basic elements of the apparatus for detecting changes in voltage drop across a medium. This basic diagram is essentially an electrical circuit 10 in which an alternating current electrical energy source 11, such as an oscillator, delivers current to a selected cell 12 thereby developing a voltage thereacross. A cell 12 is selected by an analog multiplexer 13 which includes a drive current multiplexer 13A and a voltage feedback multiplexer 13B. The cell 12 designated R is a reference cell while the cells 12 designated $S_1$-$S_N$ are sample cells.

Figure 2:
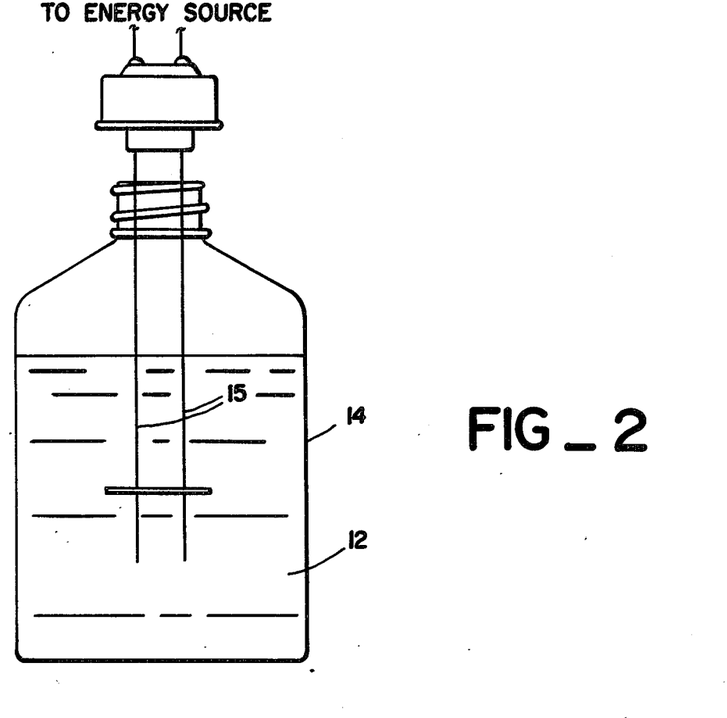
FIG. 2 is an illustration of a bottle for testing a sample medium.

The selected sample cell $S_1$-$S_N$ may be a container holding a medium which is suitable for growing of microorganisms therein. Although the apparatus preferably monitors growth of microorganisms in a growth medium, it is intended to monitor and detect metabolic activity in general in addition to microorganism growth. These activities include, but are not limited to, cell growth, whether animal or plant, monitoring protozoa, metazoa and the like, and monitoring suspensions of cellular enzymes. For the sake of clarity and by way of example only, the description of the preferred embodiment of this invention is directed to detection of microorganism growth in a growth medium. The current is delivered to the selected sample medium 12 by means of a pair of electrodes placed in the medium for galvanic contact, the electrodes being part of the circuit. In the sample medium 12 is placed, generally before the test begins, a suspected metabolic agent such as a microorganism contaminant, which is to be tested for a determination of whether microorganisms are indeed present, and possibly their identities, levels of concentration, antibiotic susceptibility, among other determinations. One convenient carrier for conducting these types of tests is what is known as a "blood bottle" for monitoring low concentrations of organisms, and which is depicted in FIG. 2. A "module" may be used to monitor large concentrations of organisms where a small volume of media is satisfactory. Sample medium 12, a selected fluid, is placed in a bottle 14 so that electrodes 15 are placed in the fluid. To receive the electrical current in the medium, the electrodes 15 are placed in the electrical circuit 10 for connection ultimately to the source 11. This type bottle is normally stoppered, but has a small opening or is puncturable so that a suspected contaminant may be inoculated into the medium in the bottle. It can be appreciated that many bottles comprising sample cells $S_1$-$S_N$ or other media carriers may be connected in the electrical circuit 10 via multiplexer 13 so that a plurality of samples may be tested. Furthermore, a bottle carrying the fluid medium may be used as the reference medium 12 designated R for a plurality of bottles by withholding any inoculants; the reference medium R may be inserted into the circuit and compared with any given sample medium $S_1$-$S_N$ for the purpose of eliminating all variables which affect the voltage changes of the media except microorganism growth. In addition, for purposes of testing, one sample may consist of more than one bottle or well appropriately wired, in series for example, to include activity in a multiplicity of wells as indicative of one sample under test. Proper computer software may be used to compare a reference with a plurality of samples which can be employed.

Returning to FIG. 1, it is noted that before the A.C. source 11 develops a voltage potential across cells 12, a programmable current driver 24 has been interposed in the electrical circuit 10. Current driver 24 receives current from the oscillator 11, but its current output to a selected cell 12 is controlled by information received from the digital control section 25. Thus, the current driver 24 is a programmable or variable current source which is controlled to deliver current to any selected sample in variable amounts depending upon input data received from the digital control section 25.

Digital control section 25, as will be more fully described, controls programmable current driver 24 which is a multiplier of the current from A.C. source 11, and, therefore, determines the amount of current sent to a selected cell 12 via multiplexer 13. Current driver 24 includes an R-2R ladder network having a plurality of resistors which are selectively coupled to the source 11 as determined by 16 bit digital control words generated by section 25. The determination of the appropriate binary information generated by section 25 to control the current driver 24 for delivery of current to the sample is illustrated by referring now to FIG. 3, taken in conjunction with FIG. 1.

Figure 3:
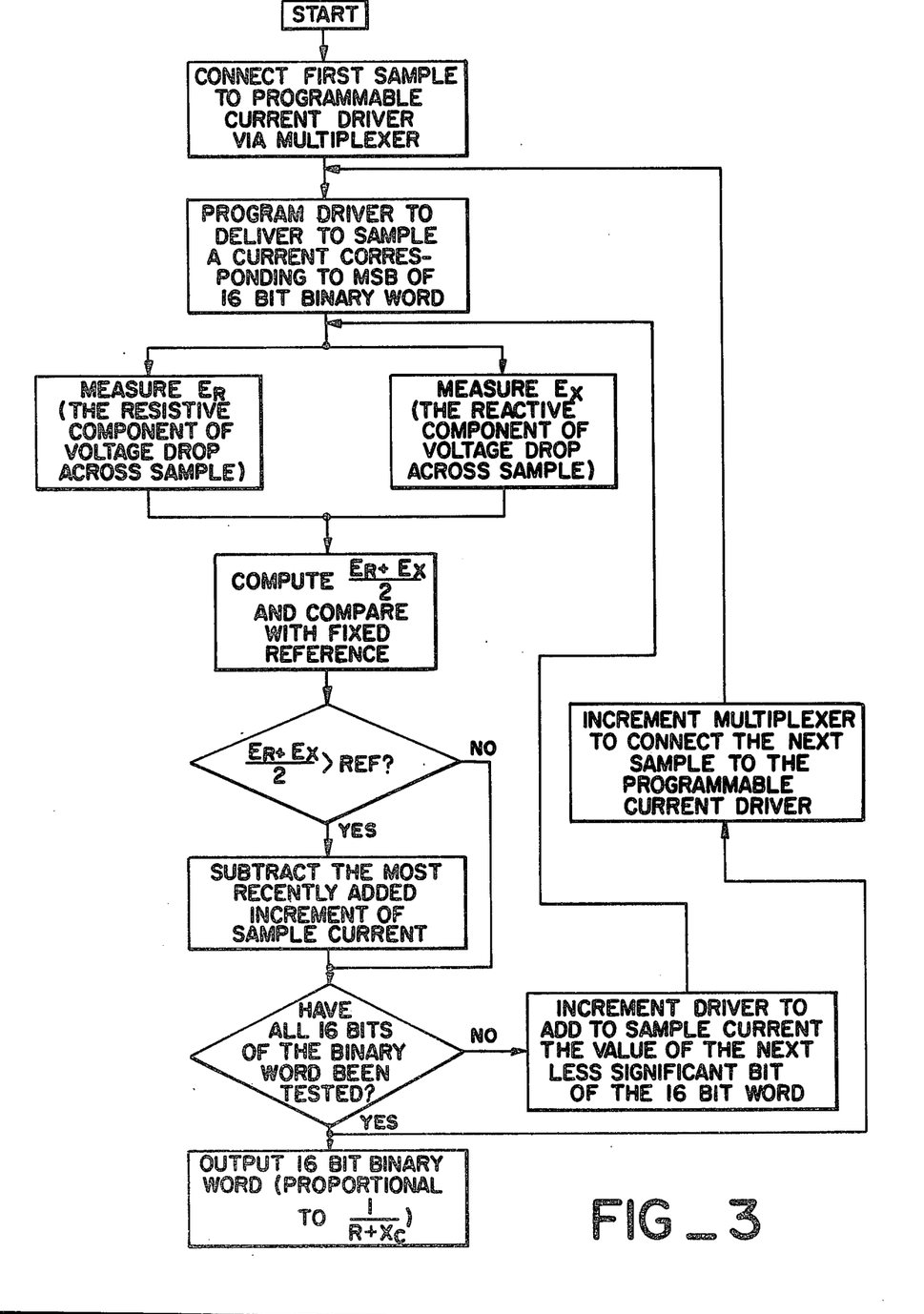
FIG. 3 is a flow chart of the measurement sequence of the inventive apparatus.

In FIG. 3, which is a simplified flow diagram of the measuring and control sequence, the initial step is to electrically connect the selected sample 12 to the programmable current driver 24 via multiplexer 13. At this stage a sixteen bit successive approximation process is initiated in digital control section 25 which will ultimately determine how much current must be delivered to sample 12 to develop a voltage drop thereacross sufficient to balance with the fixed reference output from the A.C. source 11. In the first step of this successive approximation process the digital control section 25 sends a signal to programmable current driver 24 which causes the latter to deliver to sample 12 a current corresponding to the most significant bit (MSB) value of the sixteen bit successive approximation word.

With this amount of current delivered to sample 12, a certain voltage drop will result across that sample. By the appropriate circuitry, as hereinafter described more thoroughly in conjunction with FIG. 4, the resistive component ($E_R$) and the reactive component ($E_X$) of the voltage drop across the sample are measured. The resistive component of voltage is related to the electrical resistance of the sample medium as the current passes therethrough; the reactive component of voltage is related to the capacitive and inductive values of the sample medium. Since, however, inductance is not known to play any significant role in biological-electrical characteristic measurements, it is assumed that the reactive component is due solely to capacitive considerations.

At this stage, the average voltage of the resistive and reactive components is automatically computed with the resulting value being compared with the fixed reference voltage from A.C. source 11. While the preferred apparatus and method, as exemplified herein, uses this average voltage to make a comparison with a fixed reference voltage, to be subsequently discussed, other approaches may be used. For instance, either the resistive or the reactive components, independently, may be compared with a reference voltage; or a complex entity similar to impedance, composed of both resistive and reactive components, may be employed. However, a phase shift must be reckoned with in designing the proper circuitry. It has been found that using the average voltage of resistive and reactive components for carrying out the comparison steps of this invention provides satisfactory results.

Before continuing with the flow chart of FIG. 3, attention is directed to the block diagram of FIG. 1. It is noted that from the sample, the electrical signal is broken down into two components $E_R$, the resistive, and $E_X$, the reactive after amplification and filtering. An in-phase filter 16 and a quadrature filter 18 include appropriate switching devices which separate the resistive and the reactive components, respectively, which are then fed to an averaging network 19. As indicated by its name, filter 16 separates that component of the voltage that is in phase with the current, represented by $E_R$, whereas the quadrature filter 18 separates that component that is 90° out of phase with the current, represented by $E_X$. Averaging network 19 is the electrical circuitry which is employed to average the values of resistive and reactive components of voltage of the sample at any given time during the test. A voltage amplifier 20 is provided in the circuit 10 to amplify the signal before it reaches filters 16 and 18 which require a higher amount of voltage for optimum accuracy in the circuit to be described more fully in conjunction with FIG. 4.

As seen in FIG. 1, the A.C. source 11, the oscillator, also generates a reference output signal. This reference signal is a substantially constant level of voltage and is proportional to the voltage of the oscillator. Both the reference voltage and the average of the voltage components are directed to the balance detector circuitry 21 which comprises a comparator and low pass filter. The function of the balance detector 21 is best illustrated by referring to the flow chart of FIG. 3.

After the average voltage $$(\frac{E_R + E_X}{2})$$

is computed, it is compared with the fixed reference voltage ($E_{REF}$) generated by the oscillator. By appropriate digital circuitry, the average voltage is compared with the reference voltage to determine whether the average voltage is greater than the reference voltage. If the average voltage exceeds the reference voltage, the MSB of the successive approximation circuitry 25A is reset causing the MSB increment of current fro current driver 24 to be removed since the MSB increment is too much and only less significant bit increments are needed to achieve balance. If, on the other hand, the average voltage does not exceed the reference voltage, the MSB is retained since this increment of current will be needed to achieve balance.

At this point, the digital control section 25 sends a signal to the programmable current source 24 which causes the second most significant bit value (one half of the MSB value) of current to be added to the current, if any, in sample 12. The resulting new values of $E_R$ and $E_X$ are then measured and $$(\frac{E_R + E_X}{2})$$

is compared with ($E_{REF}$) in the same manner as previously described to determine whether this increment of current is too much or too little to achieve balance. This cycle continues until all sixteen bits have been tested as determined by the digital control section 25.

When all the bits have been tested, the current driver 24 delivers a sufficient amount of current to the selected sample so that the previously defined average voltage thereacross either balances with or closely approximates the reference voltage generated by the A.C. source. This entire aproximation process is done automatically in the electrical circuit, and can be completed in about two seconds or less. After one approximation process is accomplished for one sample, multiplexer 13 selects another sample cell 12 for another approximation process similar to that already described.

It has been known for some time that the electrical characteristics such as resistance and reactance of a medium change perceptibly by the growth of microbiological organisms which may be present therein. For instance, ionized waste products from microorganisms tend to change the electrical impedance of the medium into which they are discharged. This change in electrical impedance will produce a change of voltage when the current is constant in tests where the medium is connected in a circuit with an appropriate power source. Generally, the growth of microorganisms in a medium causes a decrease in the voltage drop across the medium. These changes become more pronounced as the metabolic activity and concentration levels of microorganisms increase in the medium.

In the present invention, when the sample medium contains a microorganism contaminant, the electrical characteristics of the medium change as the microorganisms increase in number. If the electrical current remained at a constant level, the voltage across the sample would change, most likely decrease. However, the new apparatus of the present invention is concerned with keeping the voltage drop across the sample as closely balanced as possible with the fixed reference voltage. Accordingly, when microorganisms start growing in the sample, the voltage drop across the sample is adjusted, periodically, to always closely approximate the reference voltage. This adjustment is accomplished by supplying more or less electrical current to the sample as explained above. The amount of current required to make such a voltage adjustment to achieve balance with a reference represents the output of the electrical circuit 10 as seen in FIGS. 1 and 3.

The digital control section includes successive approximation and timing logic 25A, whose digital output is the 16 bit word controlling current driver 24, a digital multiplexer 25B, a serial interface 25C, address logic 25D and a command decoder 25E. Each time there is a complete run through 16 bits for a selected sample, the output of logic 25A is monitored. This output is fed through digital multiplexer 25B and serial interface 25C to a computer 26 which controls CRT display terminal 27 or a hard copy printer terminal 28. Alternatively, the output from interface 25C and be fed directly to a chart recorder (not shown) which becomes a source of collective data relating to the growth of microorganisms in a medium, and is a ready reference used to make a rapid determination that metabolic activity is occurring.

With the desirable decrease in time for making determinations relating to the presence of microorganisms, it is preferred to interface the computer 26 with the output of the circuit 25 for performing a multiplicity of tasks. Some of the functions which can feasibly be programmed into the computer in conjunction with the instant invention include, but are no means limited to, the following: a correlation of data with various sample numbers when many samples are being tested; constant monitoring of hardware and look at critical components and variables under which the tests are being performed; a selective or random monitoring of individual samples when called upon in addition to the standard successive monitoring; a detection of errors or indication of false readings; ignoring samples which are out of line with standard or expected results; possible detection algorithms, i.e., whether there is growth, time to reach a threshold concentration level, and possibly an enumeration per unit volume of the microorganisms; possible identification of the type or types of microorganisms present, or the percentage probabilities of various species of microorganisms present; types of organisms which prove susceptible to anti-metabolites, and the like. The computer 26 also can be connected to appropriate circuitry built into the system to check the reliability and proper functioning of the same, during each cycle or periodically, according to choice of the designer. Depending upon the computer capability desired, the interface circuitry can be designed accordingly as is known in that art.

The address logic 25D functions to send address information to multiplexer 13 to switch in one of the samples 12. This address information is also fed to multiplexer 25B where it is multiplexed with the digital information from logic 25A to inform the computer to which sample 12 the digital information applies. The command decoder 25E functions to decode commands from the computer 26 through interface 25C so as to, for example, start the successive approximation technique via logic 25A and generate address information via logic 25D.

One of the significant features of the present invention is its ability to handle a large plurality of samples during one test. As illustrated in FIG. 3, and as already indicated, after the 16 bit control word has all its bits tested, the output of the digital control section 25 is monitored, and the next sample is automatically connected to the current driver 24. This automatic connection is accomplished by means of address logic 25D and multiplex switches 13, which allow each sample to be sequentially tested until the complete array is exhausted, whereupon the process of testing each sample repeats itself. Thus, with the comparing and balancing features of the present invention, along with multiplexer switching capabilities, true and accurate readings of voltage across a large number of samples are achieved, with a sensitive and accurate monitoring of changes in those voltage levels to indicate growth of microorganisms in a sample medium.

An area in which large numbers of samples of media are to be tested is the culturing of blood. A system wherein over a hundred samples in bottles (similar to the embodiment of FIG. 2) or modules known in the art can be monitored during one test is readily devisable using the apparatus and techniques described above. Such system, according to choice of design, may accommodate various types of medium carriers, such as bottles, sealed measurement cells (such as described in U.S. Pat. Nos. 3,743,581 and 3,890,301), modules comprising a unitized array of chambers for media, and the like. In addition, for control over temperature and other environmental conditions, and to produce a more rapid determination of microorganism presence in the medium, the apparatus of this invention may include one or more incubators. By heating the medium uniformly, the metabolic activity of the microorganisms is accelerated with an opportunity to make a much earlier detection.

Figure 4:
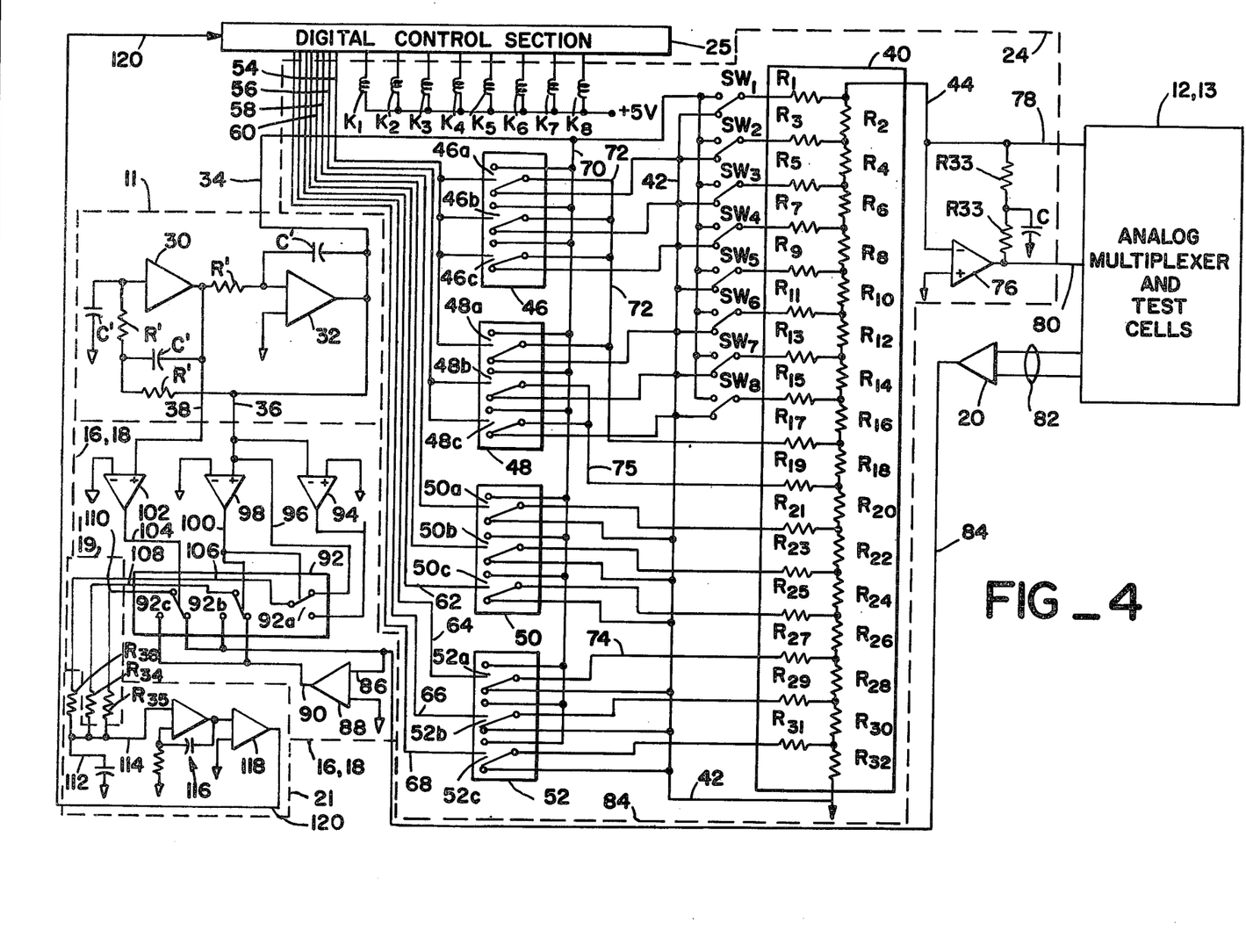
FIG. 4 is a schematic diagram depicting, by way of example only, a specific circuit which may be employed in the block diagram of FIG. 1 and the flow chart of FIG. 3.
Figure 5:
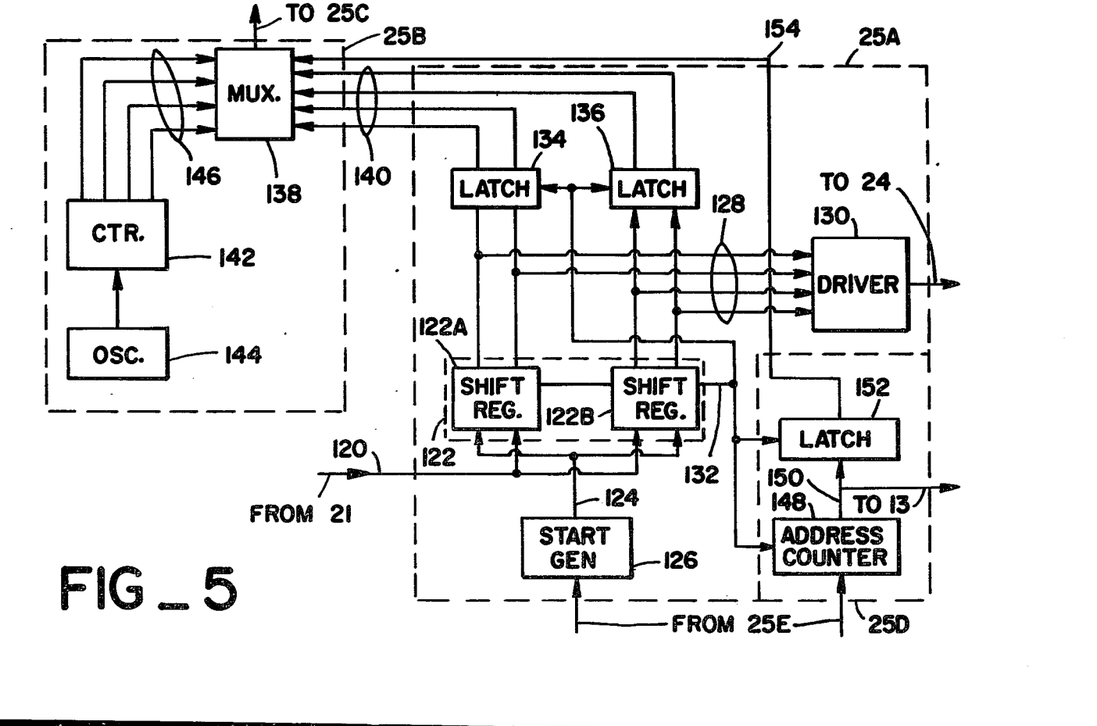
FIG. 5 is a schematic diagram depicting, by way of example, a specific circuit for various components shown in FIGS. 1 and 4.

While the selection of the electrical circuitry required to perform the functions indicated in FIG. 3 hereof in combination with the outline of FIG. 1 is not, in itself, critical, nor the essence of this invention, FIGS. 4 and 5 depict a schematic diagram of one specific circuit which satisfies the aims and features of this invention.

As shown in FIG. 4, the A.C. source 11 is a quadrature oscillator of a type well known in the art and including two operational amplifiers 30 and 32 with the output of the former coupled to the input of the latter. The various resistors R' and capacitors C' are frequency determining elements which enable the oscillator to oscillate at a predetermined fixed rate. Oscillator 11 provides a sinusoidal output on lines 34 and 36 to programmable current driver 24, and to the filters 16,18. Oscillator 11 provides another output on line 38 to the filters 16,18, which is 90° phase shifted in relation to the signals on lines 34 and 36.

The programmable current driver 24 comprises a resistive ladder network 40 having resistors $R_1$–$R_{32}$ connected as shown. The sinusoidal output on line 34 can be coupled to the odd-numbered resistors $R_1$–$R_{15}$ through the energization of eight relay coils $K_1$–$K_8$ which control, respectively, switches $SW_1$–$SW_8$. As illustrated in FIG. 4, these switches $SW_1$–$SW_8$ are in their low state connected to ground via line 42. In this position of the switches $SW_1$–$SW_8$, the output on line 34 is not coupled to any one of the odd-numbered resistors $R_1$–$R_{15}$. However, when one of the relays, for example, $K_3$, is energized, then switch $SW_3$ will change state to couple the signal on line 34 through this switch to resistor $R_5$ and then through resistors $R_4$ and $R_2$ to the output of the ladder 40 on line 44. In a similar manner, it may be seen that when any one of the relay coils $K_1$–$K_8$ is energized, the corresponding switches $SW_1$–$SW_8$ will change state to couple the signal on line 34 through any one of the corresponding odd-numbered resistors $R_1$–$R_{15}$ and ultimately out to output line 44.

Current driver 24 also includes four integrated circuits 46,48,50,52 for coupling the signal on line 34 to odd-numbered resistors $R_{17}$–$R_{31}$ of the ladder network 40. Each integrated circuit includes, respectively, solid state switching devices which may be MOSFET's. Thus, circuit 46 includes field effect transistor switches (FET's) 46a,46b and 46c, circuit 48 includes FET's 48a,48b and 48c, circuit 50 includes FET's 50a,50b and 50c, while circuit 52 includes FET's 52a,52b and 52c. Eight lines 54,56,58,60,62,64,66 and 68 are coupled, as shown, to the control inputs for these FET's so that when a signal on one of these lines is applied to a respective control input, the corresponding FET changes state.

As shown in FIG. 4, the FET's on circuits 46,48,50 and 52 are in their "low" state and connected to ground through line 42. When, for example, a gating signal is applied on line 54, the FET's 46a,46b,46c and 48a will be turned to their "high" state, i.e., the "contacts" shown for these transistors will connect to A.C. source 11 through line 34. In this condition, the signal on line 34 will be coupled to resistor $R_{17}$ through respective FET's 46a–46c which connect a line 70 to a line 72, and then to line 44 via even-numbered resistors $R_{16}$–$R_2$. In a similar manner, FET 48a couples the signal on line 34 from line 70 to the line 72 and then to resistor $R_{17}$. If, as another example, a gating signal were applied on line 64, FET 52a will be switched so as to couple the signal on line 34 from line 70 to a line 74 and thereby to resistor $R_{27}$. Based on the above discussion and the illustration of FIG. 4, it will be readily apparent that if a gating signal is applied to one of the control inputs, the corresponding FET's will couple the signal on line 34 through line 70 to the various odd-numbered resistors $R_{17}$–$R_{31}$ of the ladder 40. As can be appreciated, therefore, the current on line 44 will depend on which of switches $SW_1$–$SW_8$ and the FET's are "high" or "low". The manner in which a gating signal is applied to one of the lines 54,56,58,60,62,64,66 or 68, or in which one of the relay coils $K_1$–$K_8$ is energized, is controlled by the digital control section 25 which will be described in connection with FIG. 5.

The current signal on line 44 is fed to an operational amplifier 76 which maintains its inverting input at virtual ground while forcing the current on line 44 through sample 12 via line 78, multiplexer 13 and line 80. The two resistors $R_{33}$, together with capacitor C, shown between line 78 and line 80 coupled to amplifier 76, provide a D.C. feedback path with a very high impedance to the A.C. portion of the signal on line 78 so that only the A.C. signal is fed to the multiplexer and test cells 12,13.

The voltage developed across one of the multiplexed cells by the current signal on line 78 is then fed back over lines 82 to the voltage amplifier 20, which is of a type well known in the art. The amplified voltage is then fed from amplifier 20 over line 84 to filters 16,18. The signal on line 84 is fed over line 86 as an input to a phase inverter 88 whose output is produced on a line 90. The signals on lines 84 and 90 are fed into a switching network 92 which functions to provide signals $E_R$, $E_X$ and the reference voltage from source 11.

Other signals fed to the switching network 92 include the output of a phase inverter 94 whose one input is the signal on line 36, a non-inverted signal from line 36 on line 96, and the output of a comparator 98 on line 100. Comparator 98 receives the sinusoidal signal on line 36 and converts this signal to a square wave output on line 100. The comparator 98 functions in a standard manner to provide a square wave transition each time the sinusoidal input goes through a zero crossing, this pulse corresponding to the polarity of the sinusoidal input.

Switching network 92 also receives the output of another comparator 102 on line 104, the input to this comparator being the 90° phase shifted sinusoidal signal on line 38. As with comparator 98, comparator 102 provides a square wave output, but this output is 90° phase shifted in relation to the square wave output on line 100.

The switching network 92 includes three switches 92a, 92b and 92c which also may be MOSFET's. Network 92 also includes an output line 106 connected to switch 92a and which supplies the reference voltage, an output line 108 connected to switch 92b and which supplies the signal $E_R$, and an output line 110 connected to switch 92c and which supplies the signal $E_X$. As indicated in FIG. 4, switch 92a is caused to change its state by the signal on line 100, while switches 92b and 92c change their state in response to the signals on lines 100 and 104 respectively.

Switching network 92 operates in the following manner. To provide the reference voltage output on line 106, when the output on line 100 is negative, corresponding to the negative half cycle of the sinusoidal input on line 36, the contacts of switch 92a are in the position shown. Accordingly, a negative sinusoidal output is applied from line 96, through switch 92a, to line 106. On the next half cycle, the output on line 100 will be positive to cause the contacts on switch 92a to switch state to connect the output of phase inverter 94 to line 106. At this time of the next half cycle, the positive cycle of the sinusoidal wave on line 36 will be phase inverted by inverter 94, thereby providing a negative half cycle on line 106. On the next negative half cycle of the input to comparator 98, switch 92a again will change state to the state shown in FIG. 4 so that another negative half cycle will be output on line 106. This switching of switch 92a continues with each half cycle of the input signal on line 36 so that it can be seen that the output on line 106 is a rectified negative signal comprising the reference voltage. It should be noted that in FIG. 1 the reference voltage is shown as coming from the source 11 while in FIG. 4 it is shown on line 106 as being output from the filters 16,18. The former was shown merely for ease of explanation of the invention, while FIG. 4 shows the actual source of this reference signal.

To obtain the signal on line 108, switch 92b constantly changes state with each zero crossing of the signal on line 36 in response to the gating signal on line 100. With switch 92b in the state shown in FIG. 4, the inverted signal on line 90 is fed through switch 92b to line 108. On the next half cycle of the signal on line 36, switch 92b changes state to couple the non-inverted signal on line 84 to output line 108. The switching of switch 92b is in phase with the signal on line 36 and hence, the signal on line 34, so that the component of the voltage from amplifier 20 which is in phase with the current on line 34 is separated out. This component voltage is the resistive component $E_R$ of the cell 12 being tested.

To obtain the signal on line 110, switch 92c constantly changes state 90° phase shifted from each zero crossing of the signal on line 34 in response to the signal on line 104. With the switch 92c in the state shown in FIG. 4, the non-inverted signal on line 84 is fed through switch 92c to line 110. On the next half cycle of the signal on line 38, switch 92c changes state to couple the phase inverted signal on line 90 to output line 110. The switching of switch 92c, being 90° phase shifted from the signal on line 34, separates out the component of the voltage from amplifier 20 that is at quadrature with the signal on line 34. Hence, this voltage component $E_X$ on line 110 is the voltage across the capacitive component of the cell 12 being tested.

The positive outputs on lines 108 and 110 are fed through respective resistors $R_{34}$ and $R_{35}$ which function as the averaging network 19 while the rectified negative output on line 106 is fed through a resistor $R_{36}$. These three resistors $R_{34}$, $R_{35}$ and $R_{36}$ are connected to a summing junction 112 which forms the balance detector 21. The signal on line 114 will be 0 when the average of $E_R$ and $E_X$ is balanced with the reference voltage. The signal on line 114 is filtered by a low pass filter 116 which provides an output to a comparator 118. When the signals are not balanced, comparator 118 produces an output on line 120 that is then fed to the digital control section 25 which causes a change of state in one of the switches $SW_1$–$SW_8$ or one of the FET's in switching circuits 46,48,50 or 52.

As an example of the operation of the structure of FIG. 4, assume that the output on line 120 indicates an above balance condition (i.e.

$$\frac{E_X + E_R}{2}$$

is greater than $E_{REF}$), and that in the previous step switch $SW_1$ was closed to couple the output on line 34 to line 44. The digital control section 25 will produce a signal to energize relay $K_2$ via the +5 volt supply and deenergize relay $K_1$. Accordingly, switch $SW_1$ will return to the state shown in FIG. 4 and switch $SW_2$ will switch states to couple the signal on line 34 through this switch, then through resistors R₃ and R₂ to the output on line 44. The current on line 44, as determined by the ladder network 40, will then be fed to a selected sample cell via line 78 to develop a voltage across this cell. This voltage will then be fed back over lines 82, amplified by amplifier 20 and fed to switching network 92 to develop signals $E_R$ and $E_X$ as already described. These two signals will then be averaged via resistors R₃₅ and R₃₆ and compared to the reference voltage developed on line 36. If a below balance condition exists (i.e., $$\frac{E_X + E_R}{2}$$

is less than $E_{REF}$), the signal on line 120 causes K₂ to remain energized and in either event the same process will be repeated for each of the remaining steps of the successive approximation sequence.

In reference to FIG. 5, timing logic 25A includes a successive approximation register 122 comprising two eight bit shift registers 122A and 122B. The register 122 is initially activated by a signal on line 124 from a start signal generator 126 which may be turned on by a signal from the decoder 25E. The registers 122A and 122B receive the signal from balance detector 21 over line 120 as shown. The output of the successive approximation register 122 is fed over four lines 128 to a driver 130, with each line 128 representing four bits. Shift register 122B also provides an output on line 132 after 16 bits for a selected cell 12 have been tested. This signal on line 132 is fed to two latches 134 and 136 which latch the information in the successive approximation register 122 after this 16 bit testing. Driver 130 includes transistor-transistor logic (TTL) having a plurality of transistors which, when energized, close a circuit through respective relays K₁-K₈ and the MOS-FET's on circuits 46,48,50 and 52.

The digital multiplexer 25B includes a multiplexer 138 which selects the data in latches 134 and 136 via lines 140. A counter 142 which counts the output of an oscillator 144 activates the multiplexer 138 over lines 146 to select the latched data at preset times.

The address logic 25D includes an address counter 148 which provides a seven bit address identifying any one of 128 sample cells to analog multiplexer 13 via line 150. The address in counter 148 is stored in a latch 152 and then incremented by one after the signal on line 132 is produced. The data in latch 152 is also fed to the multiplexer 138 via line 154.

In operation, upon testing of the first cell 12, start generator 126 is enabled and a signal shifted over line 124 into the first stage of register 122A. This signal is then fed to driver 130, so that transistors in the driver 130 are energized to close a circuit through relay K₁. After the balance testing operation is performed for the MSB, as described above, the signal on line 120 is fed into the first stage of register 122A with the signal from generator 126 formerly in the first stage shifted down to the second stage. The data in the successive approximation register 122 is then fed to driver 130 which activates suitable transistors to close a circuit through relay K₂. After the balance testing operation again is performed, the register 122 again shifts down one stage to receive any information on line 120. Again, the data now stored in register 122 is fed to driver 130 to activate other transistors for energizing relay K₃. This process continues for the 16 bits stored in register 122 and, at the end of this testing of the 16 bits, register 122B provides a signal over line 132. As a result, the 16 bit data stored in register 122 for the particular cell being sampled, is stored in latch 134 and 136 and then fed via multiplexer 138 to the serial interface 25C and then to computer 26 which processes this data for such cell. At the same time, the data in the address counter 148 is latched in latch 152 and fed over line 154 through multiplexer 138 to the serial interface 25C and ultimately to the computer 26, this address information defining the particular cell being sampled. Also, address counter 148 is incremented by one to address a new cell 12, this address data being fed to the analog multiplexer 13 to close the switches in drive current multiplexer 13A and voltage feedback multiplexer 13B for another 16 bit testing cycle for a new cell. As may be appreciated, by updating counter 148 through 128 addresses and sequentially testing the 16 bits in register 122, the voltage feedback information for each cell can be obtained to detect microbial growth in each sample.

What is claimed is:

1. Apparatus for detecting metabolic activity in a growth medium comprising;
   a source of electrical energy;
   means for applying said electrical energy through a sample of growth media containing a suspected metabolic agent therein and developing a voltage thereacross, said voltage changing in response to metabolic activity therein;
   means for generating an electrical reference signal in the form of a substantially constant voltage;
   means for measuring the voltage developed across said sample and comparing the same with said reference voltage;
   first means for adjusting the voltage developed across said sample to closely approximate or balance the same with said reference voltage; and
   means for monitoring the balancing adjustment of said voltage developed across said sample to correlate said adjustment with a detection of metabolic activity therein.

2. An apparatus as defined in claim 1 wherein said means for measuring the voltage developed across said sample and for comparing the same with said reference voltage includes an electrical circuit means for measuring the voltage developed across said sample and determining whether the voltage developed across said sample is greater than said reference voltage.

3. An apparatus as defined in claim 1 wherein said measuring means includes means for measuring both resistive and reactive components of said voltage developed across said sample.

4. An apparatus as defined in claim 3 wherein said resistive and reactive components measuring means includes means for measuring the average of said resistive and reactive components of said voltage developed across said sample, said average being compared in value to said reference voltage.

5. An apparatus as defined in claim 3 wherein the measuring means is responsive to the impedance of said sample, said impedance being a function of both resistive and reactive components of said voltage developed across said sample.

6. An apparatus as defined in claim 1 wherein said means for applying said electrical energy through said sample comprises adjustable means for applying selected amounts of electrical current through said sample and second means for adjusting said adjustable means to cause the voltage developed across said sample to closely approximate said generated reference voltage.

7. An apparatus as defined in claim 6 wherein said first means for adjusting comprises a successive approximation register means, responsive to data input from said measuring and comparing means, for providing binary data, said second adjusting means including means, responsive to said binary data, for changing said adjustable means to produce a selected amount of electrical current, applied through said sample, which is directly proportional to said reference voltage times a quantity identified by said binary data.

8. An apparatus as defined in claim 7 wherein said adjustable means comprises an R-2R ladder network and switches connected to said ladder, and said second adjusting includes means for electrically and automatically closing a number of said switches.

9. An apparatus as defined in claim 1 wherein said first means for adjusting includes means to make said balancing adjustment periodically thereby providing a source of collective data on the metabolic activity therein.

10. An apparatus as defined in claim 1 which further includes means for connecting a plurality of samples of growth media to said source of electrical energy.

11. An apparatus as defined in claim 10 wherein said means for connecting a plurality of said samples includes means for connecting each sample in succession, said measuring means including means for measuring the voltage developed across each sample and comparing the same to said reference voltage, and said connecting means, upon the completion of said succession, repeating said succession to accumulate collective data on the metabolic activity in each sample.

12. An apparatus as defined in claim 11 wherein said means for connecting is a multiplex switching device.

13. An apparatus as defined in claim 1 wherein said means for monitoring said voltage adjustment is an electrical computer which is programmed to indicate when metabolic activity in said sample medium has occurred.

14. An apparatus as defined in claim 1 wherein said means for monitoring said voltage adjustment is a chart recorder which plots said adjustment.

15. An apparatus as defined in claim 1 which further includes means to induce metabolic activity in said growth medium.

16. An apparatus as defined in claim 15 wherein said metabolic activity inducing means is an incubator for providing heat to said growth medium.

17. An apparatus as defined in claim 1 wherein the metabolic activity to be detected is microorganism growth in the sample medium.

18. Apparatus for adjusting voltage developed across a medium comprising;
a source of electrical energy;
means for applying said electrical energy through a sample medium and developing a voltage thereacross, said voltage developed thereacross being susceptible to changes in the medium;
means for generating an electrical reference signal in the form of a voltage;
means for measuring the voltage developed across said sample and comparing the same with said reference voltage;
means for adjusting the voltage developed across said sample medium to closely approximate or balance the same with said reference voltage when the voltage developed across said sample is in an amount different from said reference voltage; and
means for indicating the amount of voltage adjustment across said sample medium.

19. Apparatus for providing information about a characteristic of a test sample by determining variations of an electrical signal, the variations being responsive to the sample, comprising:
a source means of electrical energy for applying said electrical signal to said test sample;
means for determining a first value of a first property of the applied electrical signal as affected by said sample;
means for generating a second reference value of said first property;
means for comparing said first value of said first property with said reference value of said first property;
means for varying a third value of a second property of the applied electrical signal to effect a predetermined relationship between said first value and said reference value of said first property; and
means for generating an output signal which is representative of said third value of said second property which is varied to effect said predetermined relationship, whereby said output signal provides information about the characteristic of said sample.

20. An apparatus as defined in claim 19 wherein said determining means includes means for detecting a voltage property of said electrical signal, and said varying means includes means for regulating a current property of said electrical signal.

21. In combination, an apparatus for detecting metabolic activity in a growth medium and means for holding said growth medium with a suspected metabolic agent contained therein, said holding means including a pair of spaced electrodes for contact with said medium placed therein, said apparatus comprising:
a source means of electrical energy, said source means being in electrical circuit with said pair of electrodes in said holding means for passing said energy through said medium whereby a voltage is developed thereacross;
means in said circuit for generating an electrical reference signal in the form of a substantially constant voltage;
means for measuring the voltage developed across said growth medium and comparing the same with said reference voltage;
means for adjusting the voltage developed across said growth medium which changes in response to metabolic activity therein to closely approximate or balance the same with said reference voltage; and
means for monitoring the voltage adjustment across said growth medium to correlate said adjustment with a detection of metabolic activity therein.

22. A combination in accordance with claim 21 which further includes a plurality of means for holding growth media, and means for placing each said holding means successively in said electrical circuit with said energy source means so that the voltage developed across each of said growth media is compared, in turn, with said reference voltage for changes therein.

23. A combination in accordance with claim 21 which further includes at least one reference medium which is free of a suspected metabolic agent.

24. A combination in accordance with claim 23 which further includes means to compare the changes in voltage of said sample medium with changes in voltage of said reference medium.

25. In combination, an apparatus for adjusting a voltage developed across a sample medium and means for holding said sample medium, said medium being susceptible to changes in its electrical characteristics, said holding means including a pair of spaced electrodes for contact with said medium placed therein, said apparatus comprising:
   a source means of electrical energy, said source means being in electrical circuit with said pair of electrodes in said holding means for passing said energy through said medium whereby said voltage is developed thereacross;
   means in said circuit for generating an electrical reference signal in the form of a voltage;
   means for measuring said voltage developed across said sample medium and comparing the same with said reference voltage;
   means for adjusting said voltage developed across said sample medium to closely approximate or balance the same with said reference voltage when said voltage developed across said sample medium changes to an amount different from said reference voltage; and
   means for indicating the amount of the voltage adjustment across said sample medium;

26. A method of detecting metabolic activity in a growth medium comprising the steps of:
   applying electrical energy from a source thereof through a sample of growth media containing a suspected metabolic agent therein whereby a voltage which changes in response to metabolic activity therein is developed thereacross;
   generating an electrical reference signal in the form of a substantially constant voltage;
   measuring the voltage developed across said media and comparing the same with said reference voltage;
   adjusting the voltage developed across said media to closely approximate or balance the same with said reference voltage; and
   monitoring the voltage adjustment across said media to correlate said adjustment with metabolic activity therein.

27. A method as defined in claim 26 wherein the measuring step includes measuring the resistive component of voltage developed across said media and the reactive component of voltage developed across said media.

28. A method as defined in claim 27 wherein the measuring step includes measuring the average of the resistive and reactive components of said voltage developed across said media and comparing said average to said reference voltage.

29. A method as defined in claim 26 wherein the comparing step includes determining whether said voltage developed across said media is greater than said reference voltage.

30. A method as defined in claim 26 wherein the adjusting step includes varying electrical current across said media in a sufficient amount so that said voltage developed across said media closely approximates said reference voltage.

31. A method as defined in claim 30 wherein the step of varying the electrical current includes the step of providing a variable current source with binary information from a successive approximation register so that the electrical current from said current source across said media adjusts said voltage developed across said media to closely approximate said reference voltage.

32. A method as defined in claim 26 which further includes applying electrical energy from said energy source through a plurality of samples of growth media.

33. A method as defined in claim 32 which further includes measuring in succession the voltage developed across said samples of media, and comparing individually each measurement with said reference voltage to determine whether an adjustment is to be performed.

34. A method as defined in claim 26 wherein the monitoring step includes plotting the amount of voltage adjustment across said media by means of a recording device.

35. A method as defined in claim 26 wherein the monitoring step includes feeding information pertaining to the voltage adjustment across said media to a computer for analyzing said information and indicating when metabolic activity in said media has occurred.

36. A method as defined in claim 26 wherein the metabolic activity being detected is microorganism growth in the growth medium.

37. A method of providing information about a characteristic of a test sample by measuring an electrical property thereof which is indicative of said characteristic of said test sample comprising the steps of: applying an electrical signal to said sample; determining a first value of a first property of said applied electrical signal as affected by said sample; comparing said first value to a second reference value of said first property; varying a third value of a second property of said applied electrical signal to affect a predetermined relationship between said first value of said first property and said reference value; and generating an output signal which is representative of said third value of said second property which is varied to effect said predetermined relationship, thereby providing information about a characteristic of said test sample.

38. A method as defined in claim 37 wherein said first property of said applied electrical signal is voltage and said second property of said applied electrical signal is current.

39. A method of adjusting voltage potential of a medium comprising:
   applying electrical energy from a source through a sample of said medium susceptible to changes in its electrical characteristics, whereby a voltage is developed thereacross;
   generating an electrical reference signal in the form of a voltage;
   measuring the voltage developed across said sample medium and comparing the same with said reference voltage;
   adjusting the voltage developed across said sample medium to closely approximate or balance the same with said reference voltage when the voltage developed across said sample medium changes to an amount different from said reference voltage; and
   indicating the amount of the voltage adjustment across said sample medium.

40. Apparatus for detecting metabolic activity in a sample growth medium containing a suspected metabolic agent, comprising:
   (a) means for generating electrical current and a first reference voltage;

(b) means for adjustably applying the electrical current through the sample growth medium to develop a second voltage thereacross, the second voltage changing in response to metabolic activity;
(c) means for measuring the second voltage;
(d) means for comparing the measured second voltage with the reference voltage;
(e) means, coupled to said comparing means, for controlling said applying means to adjust the second voltage to balance the second voltage with the reference voltage; and
(f) means, coupled to said controlling means, for monitoring the control of said applying means to correlate the second voltage adjustment with the metabolic activity.

* * * * *